United States Patent
Zhang et al.

(10) Patent No.: US 11,273,091 B2
(45) Date of Patent: Mar. 15, 2022

(54) ROBOT SYSTEM FOR ORAL CAVITY AND TOOTH TREATMENT

(71) Applicants: Haizhong Zhang, Beijing (CN); Yutong Zhang, Beijing (CN); Lejun Xing, Beijing (CN); Youbai Chen, Beijing (CN); Tingting Jia, Beijing (CN); Hang Feng, Beijing (CN); Yao Duan, Beijing (CN); Xiaoguang Tian, Beijing (CN); Rui Zhao, Beijing (CN); Liang Zhu, Beijing (CN); Fanhao Meng, Beijing (CN); Bo Qiao, Beijing (CN); Zheng Zhou, Beijing (CN); Suixin Hu, Beijing (CN); Nenghao Jin, Beijing (CN); Wenjun Yu, Beijing (CN)

(72) Inventors: Haizhong Zhang, Beijing (CN); Yutong Zhang, Beijing (CN); Lejun Xing, Beijing (CN); Youbai Chen, Beijing (CN); Tingting Jia, Beijing (CN); Hang Feng, Beijing (CN); Yao Duan, Beijing (CN); Xiaoguang Tian, Beijing (CN); Rui Zhao, Beijing (CN); Liang Zhu, Beijing (CN); Fanhao Meng, Beijing (CN); Bo Qiao, Beijing (CN); Zheng Zhou, Beijing (CN); Suixin Hu, Beijing (CN); Nenghao Jin, Beijing (CN); Wenjun Yu, Beijing (CN)

(73) Assignee: PLA General Hospital of China, Beijing (CN)

(*) Notice: Subject to any disclaimer, the term of this patent is extended or adjusted under 35 U.S.C. 154(b) by 518 days.

(21) Appl. No.: 15/988,094

(22) Filed: May 24, 2018

(65) Prior Publication Data
US 2018/0271734 A1 Sep. 27, 2018

Related U.S. Application Data

(63) Continuation of application No. PCT/CN2016/000648, filed on Nov. 22, 2016.

(30) Foreign Application Priority Data

Nov. 24, 2015 (CN) .......................... 201510824318.6

(51) Int. Cl.
*A61G 15/14* (2006.01)
*A61G 15/00* (2006.01)
(Continued)

(52) U.S. Cl.
CPC .............. *A61G 15/14* (2013.01); *A61B 34/30* (2016.02); *A61C 19/00* (2013.01); *A61C 19/06* (2013.01);
(Continued)

(58) Field of Classification Search
CPC ........ A61G 15/14; A61G 15/00; A61G 15/08; A61C 19/00; A61C 19/06; A61B 34/20; A61B 34/30; A61B 2090/064
See application file for complete search history.

(56) References Cited

U.S. PATENT DOCUMENTS

4,917,603 A * 4/1990 Haack ...................... A61C 5/80
433/29
5,224,049 A * 6/1993 Mushabac .......... A61C 13/0004
700/163
(Continued)

FOREIGN PATENT DOCUMENTS

CN 202829398 U 5/2013
CN 103462706 A 12/2013
(Continued)

OTHER PUBLICATIONS

International Search Report on PCT/CN2016/000648 (parent of the present application)—with translation.
(Continued)

*Primary Examiner* — Nicholas D Lucchesi
(74) *Attorney, Agent, or Firm* — Yong Chen (57) ABSTRACT

A robot system for oral cavity and tooth treatment. The system includes a console, a seat device, a robot and a navigation device. The console includes a display device, an operating device and an emergency stop device. The seat device includes a body support portion, an orientation adjustment portion and a head fixing portion. The robot comprises a main controller, a robotic arm, a manipulator. The navigation device performs navigation inside a tooth in a root canal treatment operation according to pre-stored tooth information. The treatment instrument in the manipulator can be replaceable. The seat device can be adjusted such that a patient can face any direction between forward and downward, or lie prostrate.

13 Claims, 4 Drawing Sheets

(51) Int. Cl.
| | | |
|---|---|---|
| *A61C 19/00* | (2006.01) | |
| *A61C 19/06* | (2006.01) | |
| *A61B 34/30* | (2016.01) | |
| *A61G 15/08* | (2006.01) | |
| *A61B 90/00* | (2016.01) | |
| *A61B 34/20* | (2016.01) | |

(52) U.S. Cl.
CPC ............. *A61G 15/00* (2013.01); *A61G 15/08* (2013.01); *A61B 34/20* (2016.02); *A61B 2090/064* (2016.02)

(56) References Cited

U.S. PATENT DOCUMENTS

| | | | | |
|---|---|---|---|---|
| 5,343,391 | A * | 8/1994 | Mushabac | A61C 9/008 |
| | | | | 433/76 |
| 5,448,472 | A * | 9/1995 | Mushabac | A61C 9/006 |
| | | | | 433/70 |
| 5,545,039 | A * | 8/1996 | Mushabac | A61C 9/0053 |
| | | | | 433/215 |
| 5,562,448 | A * | 10/1996 | Mushabac | A61C 13/0004 |
| | | | | 433/215 |
| 5,593,304 | A * | 1/1997 | Ram | A61C 17/0217 |
| | | | | 433/118 |
| 5,678,894 | A | 10/1997 | Eley | |
| 7,907,166 | B2 * | 3/2011 | Lamprecht | A61B 34/37 |
| | | | | 348/43 |
| 9,675,419 | B2 * | 6/2017 | Akeel | A61C 5/30 |
| 9,962,232 | B2 * | 5/2018 | Toyoda | A61G 15/16 |
| 2005/0186533 | A1* | 8/2005 | Cohen | A61G 15/14 |
| | | | | 433/98 |
| 2005/0193451 | A1* | 9/2005 | Quistgaard | A61B 5/6843 |
| | | | | 414/1 |
| 2010/0017032 | A1* | 1/2010 | Dai | B25J 9/1697 |
| | | | | 700/251 |
| 2011/0316994 | A1* | 12/2011 | Lemchen | A61C 9/0053 |
| | | | | 348/66 |
| 2012/0190981 | A1* | 7/2012 | Harris | A61B 5/150389 |
| | | | | 600/439 |
| 2013/0039541 | A1* | 2/2013 | Inazumi | G06T 5/003 |
| | | | | 382/103 |
| 2015/0057675 | A1* | 2/2015 | Akeel | G16H 40/63 |
| | | | | 606/130 |
| 2016/0166333 | A1* | 6/2016 | Wang | A61B 90/11 |
| | | | | 600/476 |
| 2018/0078332 | A1* | 3/2018 | Mozes | A61C 1/084 |
| 2019/0038367 | A1* | 2/2019 | Ciriello | A61B 34/00 |
| 2019/0223957 | A1* | 7/2019 | Dekel | A61B 34/10 |
| 2019/0327394 | A1* | 10/2019 | Ramirez Luna | H04N 13/106 |
| 2020/0008877 | A1* | 1/2020 | Jo | A61B 34/10 |
| 2020/0054421 | A1* | 2/2020 | Mozes | A61C 5/00 |
| 2020/0289224 | A1* | 9/2020 | Johnson | A61B 34/37 |
| 2020/0315754 | A1* | 10/2020 | Ciriello | A61B 34/20 |

FOREIGN PATENT DOCUMENTS

| | | |
|---|---|---|
| CN | 105395295 A | 3/2016 |
| CN | 205126477 U | 4/2016 |
| EP | 2821024 A1 | 1/2015 |

OTHER PUBLICATIONS

Written Opinion on PCT/CN2016/000648 (parent of the present application)—with translation.

* cited by examiner

ROBOT SYSTEM FOR ORAL CAVITY AND TOOTH TREATMENT

CROSS REFERENCE TO RELATED APPLICATIONS

This application is a continuation of International Patent Application PCT/CN2016/000648, filed Nov. 22, 2016, which claims priority to Chinese Patent Application 201510824318.6, filed Nov. 24, 2015. The disclosures of these prior-filed applications are incorporated by reference herein in their entirety.

FIELD OF TECHNOLOGY

The present invention relates to a robot system for oral cavity and tooth treatment, in particular to a robot system for controlling a robot to treat a tooth.

BACKGROUND

In dental treatment procedures currently practiced, a doctor generally performs the therapy and operation manually, which requires the doctor to observe closely to perform an operation. To complete an operation, the doctor need to spend a large amount of physical energy, and need to maintain a posture for a long time, such as keeping his or her head low, among others. As a result, is prone to cause fatigue for doctors, the doctor working for a long time is easy to get tired, thus reducing operation quality.

At present, various dental handpieces are already proposed in related fields to replace the manual operation of a dentist, thereby reducing the workload of the dentist, and realizing intelligent dental treatment. In such dental handpieces, through a camera and a lighting device installed, image of a tooth in the oral cavity of a patient is transmitted to a display, and then the doctor performs an operation based on what is shown on the display. Therefore, the doctor does not need to observe the oral cavity of the patient at a short distance to perform the operation. As a result, the physical energy and stamina required of the doctor is greatly reduced for the operation, the fatigue is much lessened, and the operation quality is improved.

However, the above-described dental handpieces still have the following problems, among others: the dental handpieces comprise only an operating manipulator such as a drill bit; a doctor can only perform an operation through simple control using the manipulator, and cannot intelligently perform different types of dental procedures; the scope of application of such handpieces is narrow, and intelligent control cannot be realized.

SUMMARY

The present invention provides a robot system for oral cavity and tooth treatment. On the basis of the original dental handpiece, the present invention provides a complete robot system, wherein the system can act as an integrated dental treatment device based on which the entire operating procedure of various dental treatments can be completed. In addition, in the robot system, the manipulator, as an operating main body, comprises at least one manipulator capable of being replaced with a treatment instrument, which ensures that the robot system can be used to perform different dental treatments. Furthermore, in the robot system, the orientation of the seat can be adjusted to allow the patient to face forward or downward, or allow the patient to lie prostrate to receive a dental treatment, in which case the sprayed water in the oral cavity of the patient can naturally flow out during dental treatment instead of being left in the oral cavity, reducing the discomfort of the patient due to the dirty water.

Specifically, according to one aspect of the present invention, provided is a manipulator for treating oral cavity and teeth of a patient, comprising:

a shell, detachable and provided thereon a fixing portion and a water spray outlet, wherein the fixing portion fixes a base end of a treatment instrument on the shell;

a treatment instrument, used for treating the oral cavity and tooth of a patient, replaceable, and capable of being replaced with different treatment instruments as required by specific therapies;

a water sprayer, extending out from the water spray outlet, and used for spraying water or air with a certain pressure;

an lighting device, used for illuminating the oral cavity and tooth of the patient;

and an imaging device, disposed on the shell, for imaging the oral cavity and teeth of the patient.

Further, the treatment instruments are enclosed in the manipulator, and the selected treatment instrument extends out from the manipulator when in use.

Further, the treatment instrument comprises a laser head, an ultrasonic tooth cleaning head, a drill needle, an enlargement needle, a polishing head, and a filling material injection head or a filling and pressing head.

Further, the imaging device comprises more than two cameras configured to obtain a stereo image of the teeth.

Further, the cameras enlarge an image by 1-20 times.

Further, the manipulator further comprises an elastic flap, wherein the elastic flap is disposed on an outer periphery of the shell on one side that is provided with the treatment instrument, for preventing the tongue of the patient from touching the manipulator.

According to another aspect of the present invention, provided is a robot system for treating the oral cavity and teeth, comprising:

a main body, mounted with a controller and an actuator to control and drive the movement of the robot system;

at least one mechanical arm, having one end thereof movably connected to the main body via a joint and the other end movably connected to the manipulator via a joint portion, and comprising at least one intermediate joint portion, thus allowing the main body to control the manipulator to move freely in three-dimensional space;

any one manipulator as described above, movably connected to the mechanical arm via a joint portion; and a console, comprising an operating device and a display device, wherein the operating device transmits operation information to the main body to control and drive the movement of the mechanical arm and the manipulator; and the display device receives from the manipulator portion images from the imaging device, and displays the images via the display device or a visual observation device.

Further, the manipulator can extend, retract, incline and rotate by ±180 degrees relative to the movably connected arm.

Further, the display device comprises at least two displays, one for use by the patient, and the other for use by the doctor, wherein the display for patient is used for displaying a 2-dimensional image of the treatment for the patient, and the display for the doctor is used for displaying stereo images for the doctor.

Further, the display device further comprises two eye lenses; the two eye lenses and display for the doctor are utilized to realize stereo-imaging.

Further, the manipulator further comprises a pressure sensor for detecting a resistance encountered during treatment when the treatment instrument operates on a tooth, and transmitting the detection result to the console.

Further, the display for the doctor comprises a waveform display interface which displays the detection result of the pressure sensor.

Further, the operating device comprises at least one virtual operating handle connected to the console in a wireless or wired manner.

Further, the treatment robot system further comprises an emergency stop device for stopping the rotation of a drill bit and slowly withdrawing the manipulator.

Further, the treatment robot system further comprises a navigation device, wherein the navigation device comprises a body portion and a navigation tracker; the body portion is fixed to the robot system; the navigation tracker is connected to the robot system in a wireless or wired manner, such that the robot system can be controlled to move to observe the tooth of the patient; and according to tooth data acquired from the patient before an operation, the navigation device locates the tooth of the patient during treatment, and displays the depth and direction of the treatment instrument entering the tooth and root canal.

Further, the navigation tracker is disposed on an independent mechanical arm.

Further, the console allows setting a moving range for the manipulator according to the tooth data of the navigation device; and when the manipulator moves beyond the set moving range, the manipulator stops moving.

According to another aspect of the present invention, further provided is a seat device of the robot system for oral cavity and tooth treatment, comprising:

a body support portion, remaining in a fixed position relative to the position of the treatment robot system;

a head fixing portion, for fixing the head of a patient, so that the head of the patient is in a fixed position relative to the position of a seat portion; and.

an orientation adjustment portion, for adjusting the inclination angle of the seat portion, and enabling the patient to face downwards.

Further, the patient may face any directions between forward and downward.

According to another aspect of the present invention, further provided is a treatment couch of the robot system for oral cavity and tooth treatment, comprising:

a couch body, for a patient to lie prostrate, comprising a face exposure portion from which the face of the patient exposes downwards; and a head fixing portion, for fixing the head of the patient after the patient lies prostrate, so that the head of the patient is in a fixed position relative to the position of the couch body.

Further, the treatment couch further comprises an orientation adjustment portion for adjusting the inclination angle of the treatment couch.

Further, the manipulator of the robot system extends into the mouth of the patient from below.

The technical solution of the present invention will be further described in detail hereafter in connection with drawings and preferred embodiments of the present invention. And the beneficial effects of the present invention will be further specified.

BRIEF DESCRIPTION OF THE DRAWINGS

The drawings in the specification provide a further understanding to the present invention and constitute a part of the present invention. And the description thereof is used for explaining the present invention only, and not for unduly limiting the present invention.

DESCRIPTION OF THE EMBODIMENTS

The technical solution of the present invention will be clearly and completely described hereafter in connection with specific embodiments and corresponding drawings of the present invention. Obviously, the described embodiments are only some preferred embodiments of the present invention, but not all embodiments. Based on the embodiments of the present invention, all other embodiments obtained by those of ordinary skill in the art without inventive effort are within the scope of the present invention.

First Embodiment

Figure 1:
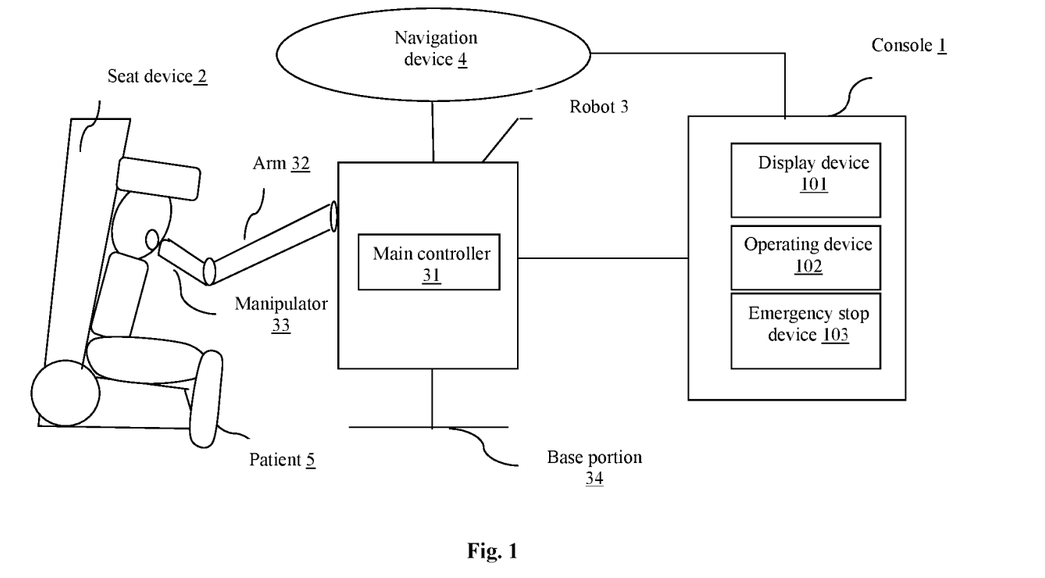
FIG. 1 is a schematic view of the robot system for oral cavity and tooth treatment according to the first embodiment of the present invention.
Figure 2:
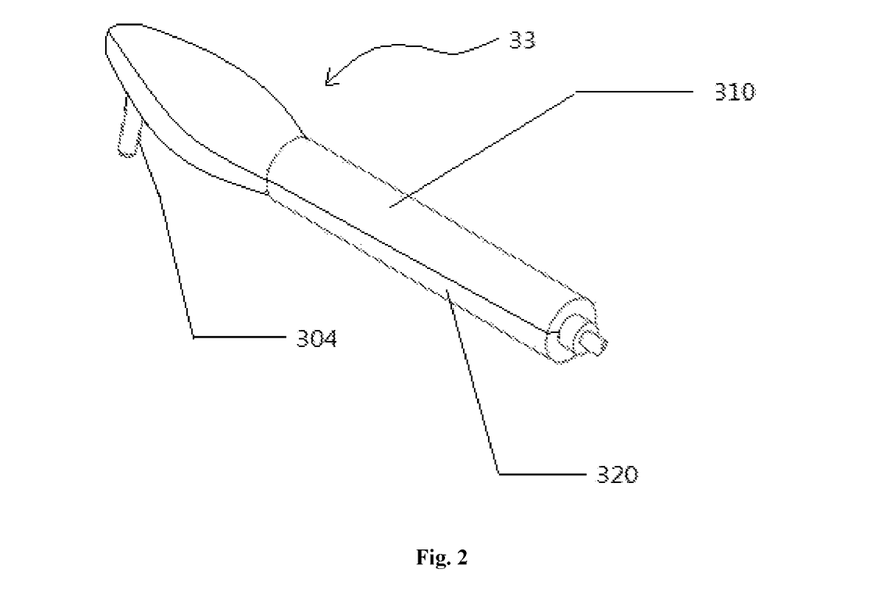
FIG. 2 is a perspective view of the manipulator of the robot system for oral cavity and tooth treatment according to the first embodiment of the present invention.
Figure 3:
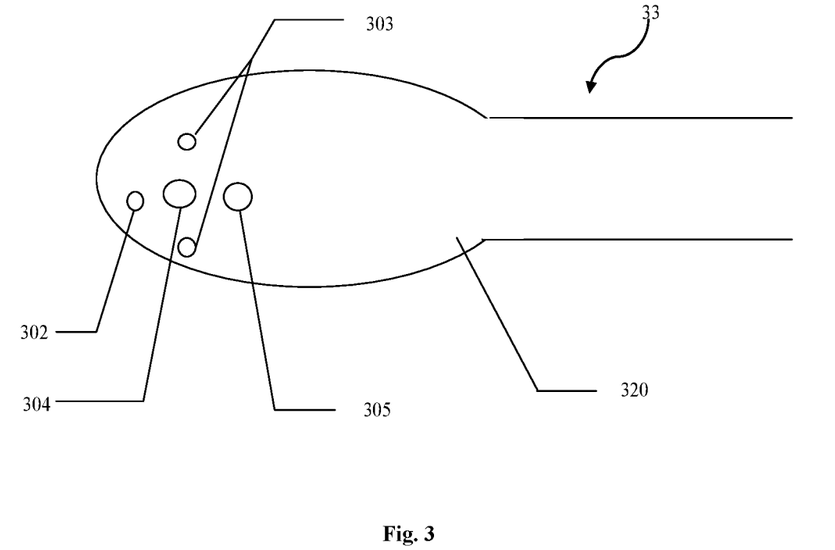
FIG. 3 is a bottom view of the manipulator of the robot system for oral cavity and tooth treatment according to the first embodiment of the present invention.
Figure 4:
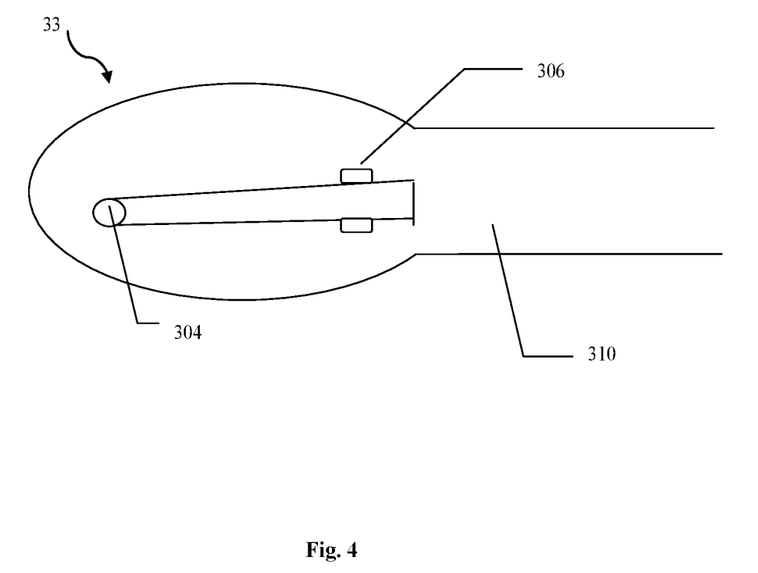
FIG. 4 is a bottom view of the internal structure of an upper shell after the shell of the manipulator of the robot system for oral cavity and tooth treatment according to the first embodiment of the present invention is disassembled.
Figure 5:
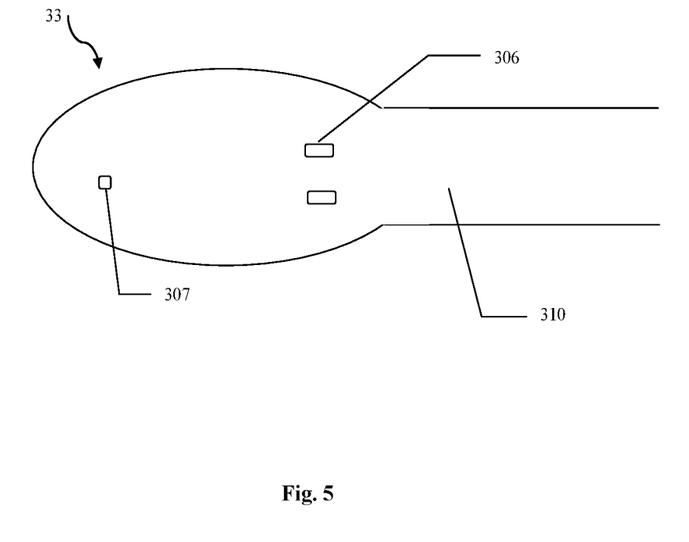
FIG. 5 is a schematic view of the robot system for oral cavity and tooth treatment according to the first embodiment of the present invention in the state as shown in FIG. 4 after the treatment instrument is removed.
Figure 6:
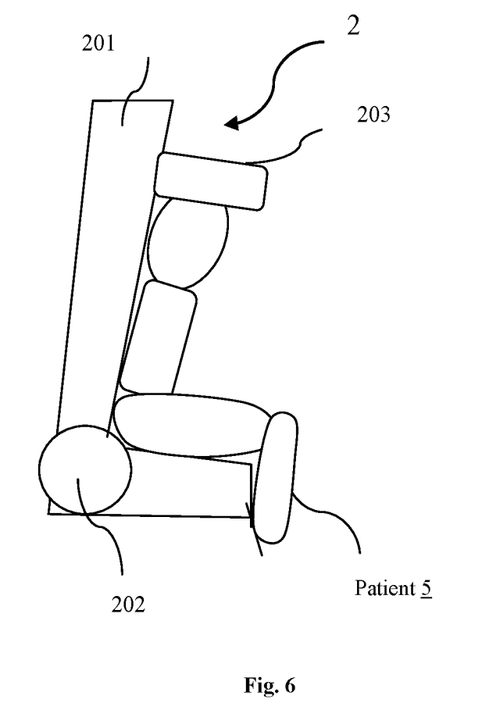
FIG. 6 is a schematic view of the seat device of the robot system for oral cavity and tooth treatment according to the first embodiment of the present invention.

The specific structure of the robot system for oral cavity and tooth treatment according to the first embodiment of the present invention will be described hereafter in connection with FIG. 1-6, wherein FIG. 1 is a schematic view of the robot system for oral cavity and tooth treatment according to the first embodiment of the present invention; FIG. 2 is a perspective view of the manipulator of the robot system for oral cavity and tooth treatment according to the first embodiment of the present invention; FIG. 3 is a bottom view of the manipulator of the robot system for oral cavity and tooth treatment according to the first embodiment of the present invention; FIG. 4 is a bottom view of the internal structure of an upper shell after the manipulator of the robot system for oral cavity and tooth treatment according to the first embodiment of the present invention is disassembled; FIG. 5 is a schematic view of the robot system for oral cavity and tooth treatment according to the first embodiment of the present invention in the state as shown in FIG. 4 after the treatment instrument is removed; and FIG. 6 is a schematic view of the seat device of the robot system for oral cavity and tooth treatment according to the first embodiment of the present invention;

As shown in FIG. 1, the robot system for oral cavity and tooth treatment according to the first embodiment of the present invention comprises a console 1, a seat device 2, a robot 3 and a navigation device 4.

Wherein, the console 1 is used for controlling the movement of robot and perform a dental treatment; the seat device 2 is used for adjusting and positioning the sitting posture of a patient, fixing the attitude of the patient during an operation, and fixing the position of the patient relative to the navigation device 4; the robot 3 is used for directly performing a dental treatment under the control of the console; and the navigation device 4 is used for storing tooth data acquired through CT scanning, and is used for tooth navigation in a complex operation, such as a root canal therapy operation. The structure of each part of the robot system will be specifically described hereafter in connection with drawings.

The console 1 comprises a display device 101, an operating device 102 and an emergency stop device 103. And the structure of each part will be specifically described hereafter.

The display device 101 comprises eye lenses and displays, wherein the eye lenses are two, and are used for observing the display result of a stereo image; the displays are at least two, namely a display for doctor use and a display for patient use, wherein the display for doctor use is used for displaying the stereo-imaging result to a doctor, such that the doctor can observe a three-dimensional image via the lenses; and the display for patient use is fixed on or in proximity to the seat device 2, and is used for displaying the video of the stereo image, such that the patient can be informed of the ongoing situation of the operation. Furthermore, the display for doctor use comprises a tooth image display interface and a waveform display interface of a pressure sensor.

The operating device 102 is used for detecting the operation of the doctor on the operating device, and transmitting operation information to the main controller 31 of the robot 3 to control the movement of the manipulator, wherein the operating device is not limited to physical operating devices such as an operating handle or a control panel, and can also be a virtual operating device such as a virtual operating handle which can be connected to the console in a wireless or wired manner.

And the emergency stop device 103 is connected to an emergency stop pedal for use by the doctor and a emergency stop button for use by the patient, and is used for detecting whether the doctor has used emergency stop pedal and whether the patient has used emergency stop button to perform an emergency stop action, and stopping the rotation of a drill bit and slowly withdrawing the manipulator in an emergency, wherein the emergency stop pedal for doctor use is disposed at the bottom of the console 1, such that the doctor can easily perform a pressing action with a foot in an emergency case; and the patient used emergency stop button is disposed on or in proximity to the seat device 2, such that the patient can easily press down the emergency stop button in an emergency case.

As shown in FIG. 6, the seat device 2 according to the first embodiment comprises: a seat portion 201, same as a traditional seat, and comprising a back rest and a base by means of which the patient can sit on the seat device; an orientation adjustment portion 202, disposed between the back rest and the base of the seat portion, and used for adjusting the angle between the back rest and the base; and a head fixing portion 203, for fixing the head of the patient, and keeping the head of the patient to be in a fixed position relative to the position of the seat portion.

Wherein, the orientation adjustment portion can adjust the head of the patient to face any directions between front and below. Therefore, when the manipulator of the robot extends into the oral cavity of the patient to spray water, the dirty water remained in the mouth of the patient can be discharged out instantly instead of being left in the oral cavity. The seat device can be utilized to ensure that no dirty water is left in the oral cavity of a patient when a dental treatment is performed on the patient, thus reducing the discomfort of the patient due to the dirty water.

The robot 3 is the main body of the entire robot system. The robot 3 comprises: a main controller 31 and a drive device thereof, for controlling and driving the entire robot to move according to the operation information transmitted by the operating device 102; at least one mechanical arm 32, movably connected to the main part of the robot 3, and adjusting the height, direction and angle of the arm of the robot, such that the manipulator can do free motion in three-dimensional space; a manipulator 33, capable of extending into the oral cavity of the patient to directly perform an operation for a to-be-operated tooth, movably connected to the arm 32 via a joint, and capable of extending, retracting, inclining and rotating by ±180 degrees relative to the movably connected arm, wherein extension and retraction mean that the manipulator moves forwards or backwards in the central shaft direction; inclination means that the central shaft of the manipulator and the central shaft of the arm have a certain angle therebetween; and rotation means circumferentially rotating around the central shaft; the specific structure of the manipulator 33 will be described later in connection with FIGS. 2-5; and a base portion 34, for supporting and positioning the robot 3.

The navigation device 4 comprises a body portion and a navigation tracker, wherein the body portion is fixed to the robot system; and the navigation tracker is connected to the robot system via another arm, such that the robot system can be controlled to move. The navigation device 4 is used for complex dental operations, such as a root canal therapy operation. In the process of tooth checking prior to a dental operation, CT scanning is performed on the tooth of the patient in advance; and the scanning result is stored in the navigation device 4, wherein the scanning result is the three-dimensional image data of the tooth; the navigation device 4 can clearly display all the details of the tooth, and display the depth and direction of the treatment instrument entering the tooth and a root canal. During the dental procedure, the navigation device 4 positions the tooth on which the procedure is to be performed via, for example, an infrared probe (not shown), and performs navigation in the whole dental operation process. The navigation device can further set a moving range of the manipulator, and enable the manipulator to stop moving when the manipulator moves beyond the moving range.

The description above is the structure of the robot system for oral cavity and tooth treatment according to the first embodiment of the present invention. And the structure of the manipulator 33 according to the first embodiment will be specifically described in connection with FIG. 2-5.

As shown in FIG. 2, the head of the manipulator 33 is in a, for example, wedge shape; and the shell of the manipulator 33 is detachable, for example, the shell can be detached in the vertical direction of the drawing into two parts, namely an upper shell 310 and a lower shell 320 in FIG. 2. The upper shell 310 and the lower shell 320 are connected via a, for example, traditional clamping structure; two clamping hooks (not shown) are disposed on one shell, and two clamping grooves (not shown) are disposed on the other shell; the clamping hooks and the clamping grooves are connected and disconnected to each other to realize the mutual connection and disconnection of the two shells.

In addition, as shown in FIG. 3, the manipulator 33 is provided with a lighting device 302, an imaging device 303, a treatment instrument 304, a water sprayer 305 and locking protrusions 306 at the head thereof. And the structure of each part will be specifically described hereafter.

The lighting device 302 is used for illuminating the oral cavity of the patient for obtaining clear images, wherein the lighting device can be one or more illumination lamps. Furthermore, the lighting device 302 is not limited to the position as shown in FIG. 3, and can be configured to be a plurality of illumination lamps around the treatment instrument.

The imaging device 303 is provided with more than two cameras for stereo-imaging, transmits the imaging result to the display device 101 in, for example, wireless manner, and displays the stereo image via the tooth image display interface of the doctor used display, thus facilitating the doctor and the patient to observe the situation of the operation, Wherein the cameras enlarge the imaging result by, for example, 1-20 times.

The treatment instrument 304 extends out from one surface at the head of the manipulator 33, for example, extends out from the largest surface of the lower shell 320, to perform an operation for the tooth of the patient. The treatment instrument can be manually replaced, namely can be manually replaced with different types of treatment instruments according to different operations, such as a laser head, an ultrasonic tooth cleaning head, a drill needle, an enlargement needle, a polishing head, and a filling material injection head or a filling and pressing head, and the like. The manipulator can also be replaced with a saliva aspirator and the like.

In addition, other than the manual replacement, the treatment instrument 304 can also be configured in other manners. For example, the treatment instrument 304 can be an integrated treatment instrument. Namely, a laser head, an ultrasonic tooth cleaning head, a drill needle, an enlargement needle, a polishing head, a filling material injection head or a filling and pressing head, and the like, can be disposed on an integrated treatment instrument according to requirements. To perform an operation, a treatment instrument corresponding to the operation is selected. The specific mechanism of selection can be a telescopic type or a rotary type, wherein the telescopic type means when the treatment instrument is not in use, the treatment instrument is retracted inside the manipulator, and when the treatment instrument is in use, the treatment instrument extends out from the manipulator; and the rotary type means when a certain treatment instrument is selected, the treatment instrument is rotated to a position above the tooth to be operated, and when the treatment instrument is not selected, the treatment instrument is moved away from the tooth to be operated.

The water sprayer 305 is disposed on a surface which is the same as the protruding surface of the treatment instrument 304, and is used for spraying water to the tooth of the patient during an operation. The water sprayer 305 is fixed relative to the above-described surface. Therefore, when the manipulator 33 is detached, the water sprayer 305 and the lower shell 320 are detached together, thus the water sprayer 305 does not affect the replacement of the treatment instrument 304. In addition, the water sprayer 305 can spray water, and can also spray air having a certain pressure to blow open the gum for the doctor to observe the state of the tooth inside the gum.

The locking protrusions 306, as shown in FIG. 4, are utilized to configure the treatment instrument 304 on the inner surface of the upper shell 310; the locking protrusions 306 are made from an elastic material, and are used for fixing the base end of the treatment instrument 304, so as to fix the treatment instrument 304 on the upper shell 310. When the treatment instrument 304 is being replaced, the locking protrusions 306 can elastically deform, such that the treatment instrument 304 can be taken out therefrom or fixed therein. The locking protrusions 306 are not limited to the above-described form, and can also adopt other forms such as a bandage, an adhesive band and the like, as long as the treatment instrument 304 can be taken out and fixed.

As shown in FIG. 5, the upper shell 310 of the manipulator 33 according to the present invention is further provided thereon with a pressure sensor 307; the pressure sensor 307 is disposed between the upper shell 310 and the treatment instrument 304, and is used for detecting a resistance encountered during treatment when the treatment instrument operates on a tooth. Furthermore, the pressure sensor 307 is electrically connected to the main controller 31, and transmits the detection result thereof to the main controller 31, and displays the result on the display device 101 of the console 1 via the waveform display interface.

In addition, the manipulator 33 according to the first embodiment of the present invention further comprises an elastic flap (not shown), wherein the elastic flap is disposed on an outer periphery of one end of the manipulator 33 provided with the treatment instrument 304 and the like, and the direction thereof is the same as that of the treatment instrument 304.

The description above is the specific structure of the manipulator 33 of the robot system for oral cavity and tooth treatment according to the first embodiment of the present invention. The specific replacement process of the treatment instrument 304 in the manipulator 33 will be described hereafter in connection with FIGS. 2-5 by using the case of replacing an ultrasonic tooth cleaning head with a drill needle as an example.

First, the clamp hooks and clamping grooves of the shell 301 are disconnected from each other to detach the shell 301. The ultrasonic tooth cleaning head is fixed to the upper shell 310 via the locking protrusions 306, and the water sprayer 305 is fixed to the lower shell 320. Therefore, when the shell 301 is detached, as shown in FIG. 4, the base end of the ultrasonic tooth cleaning head is tightly locked by the locking protrusions 306; and the water sprayer 305, the lower shell 320, and the lighting device disposed on the lower shell are disconnected from the upper shell 310 together.

Then, the base end of the ultrasonic tooth cleaning head is taken out from the locking protrusions 306; since the locking protrusions 306 are made from an elastic material, the locking protrusions 306 can deform in a direction opposite to the mutual-facing direction thereof in the take-out process, such that the distance between the two locking protrusions increases until the base end of the ultrasonic tooth cleaning head is taken out from the locking protrusions 306; the locking protrusions 306 revert to the original shape; the state after the takeout is as shown in FIG. 5.

Next, the base end of the drill needle is pressed into the locking protrusions 306; in the pressing process, the locking protrusions 306 can deform in a direction opposite to the mutual-facing direction thereof, such that the distance between the two locking protrusions increases until the drill needle is pressed into the locking protrusions 306; and the locking protrusions 306 revert to the original shape.

Finally, the head of the drill needle is aligned to the lower shell 320 to adjust and position the drill needle; then the clamp hooks and the clamping grooves are used to lock the upper shell 310 and the lower shell 320 together to complete the replacement process of the treatment instrument 304.

Second Embodiment

Figure 7:
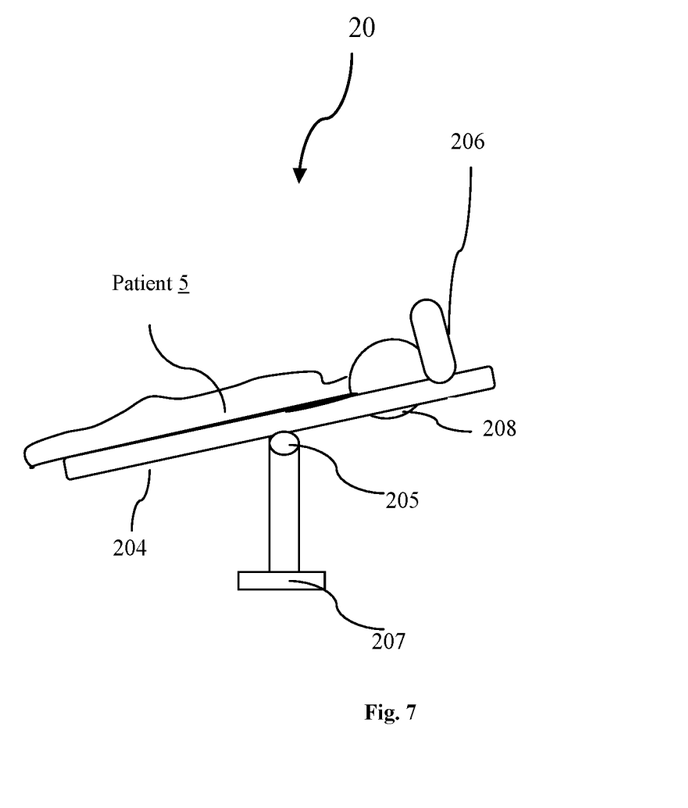
FIG. 7 is a schematic view of the treatment couch of the robot system for oral cavity and tooth treatment according to the second embodiment of the present invention.

FIG. 7 is a schematic view of the treatment couch 20 of the robot system for oral cavity and tooth treatment according to the second embodiment of the present invention. Different from the seat device 2 in the first embodiment, the second embodiment comprises a treatment couch 20. The other components in the second embodiment of the present invention are the same as those in the first embodiment, thus the description of such part of components will not be repeated.

The second embodiment of the present invention comprises a treatment couch 20, the treatment couch 20 comprising a couch body 204, a head fixing portion 206, an orientation adjustment portion 205, and a base 207, wherein the couch body 204 is a horizontal or approximately horizontal operating table on which the patient can lie prostrate; the couch body 20 is provided with a face exposure portion 208 at one end adjacent to the robot, and the face of the patient can expose from the face exposure portion 208; the head fixing portion 206 is disposed at the top of the head of the patient, thereby keeping the head of the patient to be in a fixed position relative to the position of the couch body 20; the orientation adjustment portion 205 is connected to the couch body 204 and the base 207, enabling the angle of the couch body 204 in the horizontal direction to be adjustable; and the base 207 supports the entire treatment couch 20, and is movably connected to the orientation adjustment portion 205.

In the treatment couch 20, the patient faces downwards. Therefore, in the robot system for oral cavity and tooth treatment, as in the first embodiment, the navigation device 4 is rotated to below of the patient via the movable arm, such that the tooth of the patient can be scanned. Furthermore, the manipulator is moved to the front of the patient face under the control of the console 1, and extends into the mouth of the patient from below.

In addition, in the robot system for oral cavity and tooth treatment according to the second embodiment, the display for patient use is disposed below the couch body 204, such that the patient can view the display.

The patient can lie prostrate on the treatment couch 20 of the second embodiment. When the water sprayer sprays water into the oral cavity of the patient, the dirty water can automatically flow out from the oral cavity, thus avoiding the discomfort due to the dirty water.

The description above is the robot system for oral cavity and tooth treatment according to the first embodiment and second embodiment. And the specific operating process of the entire system will be described hereafter in connection with a specific example according to the structure of the robot system for oral cavity and tooth treatment in the first embodiment and second embodiment.

(I) The operating process of the robot system during a tooth cleaning operation will be described hereafter in connection with the specific structure of the robot system for oral cavity and tooth treatment in the above-described embodiments.

Step S1, after the patient sits down, utilizing the head fixing portion of the seat device 2 to fix the head of the patient relative to the seat device.

Step S2, installing an ultrasonic tooth cleaning head as a treatment instrument according to the above-described treatment instrument replacement steps.

Step S3, utilizing the console 1 to control the robot 3. First, positioning the manipulator of the robot 3 in proximity to the to-be-operated tooth; then utilizing the eye lenses and the display device 101 to observe the stereo-imaging result of the to-be-operated tooth; utilizing the operating device 102 to control the position of the ultrasonic tooth cleaning head according to the result, and operating the ultrasonic tooth cleaning head to clear off the tartar on the surface of the tooth to clean the tooth. In the present example, in the process of controlling the ultrasonic tooth cleaning head to remove the tartar, the water sprayer is used to clean the tooth during operation.

Step S4, after the tooth is cleaned, controlling the manipulator 33 to withdraw from the oral cavity of the patient via the operating device 102, detaching the drill bit from the manipulator, and sterilizing the drill bit under a high temperature for use next time.

(II) The operating process of the robot system during a tooth root canal therapy operation will be described hereafter in connection with the specific structure of the robot system for oral cavity and tooth treatment in the first embodiment and second embodiment.

Step S1, prior to an operation, performing CT scanning on the tooth, and storing the scanning data in the navigation device 4.

Step S2, after the patient sits down, utilizing the head fixing portion of the seat device 2 to fix the head of the patient relative to the seat device.

Step S3, installing a drill bit as a treatment instrument according to the above-described treatment instrument replacement steps.

Step S4, utilizing the console 1 to control the robot 3, and positioning the manipulator of the robot 3 in proximity to the to-be-operated tooth.

Step S5, observing the stereo-imaging result of the to-be-operated tooth and the display result of the navigation system via the display device 101, and controlling the drill bit to remove the diseased part of the tooth; observing the waveform display result of the pressure sensor and the display result of the navigation system, determining that the diseased part of the to-be-operated tooth is completed removed, and controlling the water sprayer 305 to spray water for cleaning in the process of observation.

Step S6, utilizing the above-described treatment instrument replacement method to replace the drill bit with an enlargement needle, observing the stereo-imaging result of the to-be-operated tooth and the display result of the navigation system via the display device 101, controlling the enlargement needle to remove the diseased part in the root canal, and sterilizing.

Step S7, utilizing the above-described treatment instrument replacement method to replace the enlargement needle with a filling material injection head, filling the root canal and the tooth with the diseased parts removed with different materials, and completing the root canal therapy.

Step S8, controlling the manipulator 33 to withdraw from the oral cavity of the patient via the operating device 102, and detaching the filling material injection head from the manipulator.

The description above is the specific operating process of the robot system for oral cavity and tooth treatment according to the present invention. The other operation processes, such as a dental prosthesis operation, can be performed by adopting a corresponding treatment instrument with the steps similar to the steps above, and the specific description is omitted.

The robot system for oral cavity and tooth treatment according to the first embodiment and the second embodiment and the specific operating processes thereof provide a complete dental treatment robot system, and realize integrated processing of various dental treatments. Furthermore, the specific configuration of the seat device ensures that the dirty water in the oral cavity of a patient can naturally flow out during dental treatment instead of being left in the oral cavity, thus reducing the discomfort of the patient due to the dirty water.

The descriptions above are only the embodiments of the present application, but not intended to limit the present invention. For example, the manipulator 33 can comprise more than two detachable shells and the like. For a person skilled in the art, the present invention may have various modifications and variations. Any modifications, equivalent substitutions, improvements and the like within the spirit and principles of the present invention are all intended to be included within the scope of the claims of the present invention.

What is claimed is:

1. A manipulator for oral cavity and tooth treatment, comprising:
   a shell, detachable and provided thereon with a fixing portion and a water spray outlet, wherein the fixing portion fixes a base end of a treatment instrument on the shell;
   a treatment instrument, used for treating the oral cavity and tooth of a patient, replaceable, and capable of being replaced with different treatment instruments according to specific requirements for treatment, and wherein the treatment instrument can be retracted in the manipulator and can extend out from the manipulator when in use;
   a water or air sprayer, extending out from the water spray outlet, for spraying water or air having a certain pressure;
   a lighting device, for illuminating the oral cavity and tooth of the patient; and
   an imaging device, disposed on the shell, for imaging the oral cavity and tooth of the patient.

2. The manipulator as claimed in claim 1, wherein the treatment instrument is selected from the group consisting of a laser head, an ultrasonic tooth cleaning head, a drill needle, an enlarge needle, a polishing head, a filling material injection head, and a filling and pressing head.

3. The manipulator as claimed in claim 1, wherein the imaging device comprises more than two cameras configured to stereo-image a tooth.

4. The manipulator as claimed in claim 3, wherein the cameras enlarge an image by 1-20 times.

5. A robot system for oral cavity and tooth treatment, comprising:
   a main body, mounted with a controller and an actuator to control and drive the robot system to move;
   at least one arm, having one end thereof movably connected to the main body via a joint portion and another end movably connected to a manipulator of claim 1 via a joint portion, and comprising at least one intermediate joint portion, thus allowing the main body to control the manipulator to do free motion in three-dimensional space;
   and a console, comprising an operating device and a display device, wherein the operating device transmits operation information to the main body to control and drive the movement of the at least one arm and the manipulator; and the display device receives from the manipulator images from the imaging device, and displays the images via the display device or a visual observation device.

6. The robot system as claimed in claim 5, wherein the manipulator can extend, retract, incline and rotate by ±180 degrees relative to the movably connected at least one arm; and the manipulator further comprises a pressure sensor, for detecting a resistance encountered during treatment when the treatment instrument operates on a tooth, and transmitting a detection result of the resistance to the console.

7. The robot system as claimed in claim 6, wherein the display device comprises at least a display for use by a patient and a display for use by a doctor; the display for use by the patient is used for displaying a two-dimensional treatment image for the patient; the display device further comprises two eye lenses; wherein the two eye lenses and the display for use by the doctor are utilized to perform stereo-imaging; and the display for use by the doctor comprises a waveform display interface for displaying a detection result of the pressure sensor.

8. The robot system as claimed in claim 5, wherein the operating device comprises at least one virtual operating handle connected to the console in a wireless or wired manner.

9. The robot system as claimed in claim 5, further comprising an emergency stop device for stopping the movement of the treatment instrument and slowly withdrawing the manipulator.

10. The robot system as claimed in claim 9, wherein the emergency stop device comprises an emergency stop device for use by the doctor and an emergency stop device for use by the patient.

11. The robot system as claimed in claim 5, further comprising a navigation device, wherein the navigation device comprises a body portion and a navigation tracker; wherein the body portion is fixed to the robot system; wherein the navigation tracker is connected to the robot system in a wireless or wired manner, such that the robot system can be controlled to move to observe a tooth of the patient; and wherein according to tooth data acquired from the patient before an operation, the navigation device locates the tooth of the patient during treatment, and displays the depth and direction of the treatment instrument entering the tooth and a root canal.

12. The robot system as claimed in claim 11, wherein the navigation tracker is disposed on an independent mechanical arm.

13. The robot system as claimed in claim 11, wherein the console is configured to set a moving range of the manipulator according to the tooth data of the navigation device, such that the manipulator does not move beyond the set moving range.

* * * * *